(12) United States Patent
Sun et al.

(10) Patent No.: US 9,508,402 B2
(45) Date of Patent: Nov. 29, 2016

(54) READOUT DEVICE, DUAL-FUNCTION READOUT DEVICE, AND DETECTING CIRCUIT THEREOF

(71) Applicant: National Chi Nan University, Puli, Nantou (TW)

(72) Inventors: Tai-Ping Sun, Jhongli (TW); Yi-Chuan Lu, Lieyu Township, Kinmen County (TW); Tsung-Shuo Kao, Kaohsiung (TW)

(73) Assignee: NATIONAL CHI NAN UNIVERSITY, Puli, Nantou (TW)

(*) Notice: Subject to any disclaimer, the term of this patent is extended or adjusted under 35 U.S.C. 154(b) by 178 days.

(21) Appl. No.: 14/258,184

(22) Filed: Apr. 22, 2014

(65) Prior Publication Data

US 2015/0145539 A1 May 28, 2015

(30) Foreign Application Priority Data

Nov. 27, 2013 (TW) .............................. 102143250 A

(51) Int. Cl.
*G11C 7/10* (2006.01)
*G01J 1/44* (2006.01)
(Continued)

(52) U.S. Cl.
CPC ................ *G11C 7/1051* (2013.01); *G01J 1/44* (2013.01); *H04N 5/357* (2013.01); *H04N 5/378* (2013.01); *H04N 5/3745* (2013.01); *A61B 5/0531* (2013.01); *A61B 5/7225* (2013.01);
(Continued)

(58) Field of Classification Search
CPC ....... G01R 27/02; G01R 27/14; G01L 1/205; G11C 7/1051; G01J 1/44

USPC ........................................................ 324/691
See application file for complete search history.

(56) References Cited

U.S. PATENT DOCUMENTS 3,470,318 A * 9/1969 Broderick ......... H01L 27/14681
257/E27.149
3,488,636 A * 1/1970 Dyck ................... G11C 13/047
250/208.3
(Continued)

FOREIGN PATENT DOCUMENTS

| TW | 201212510 A1 | 3/2012 |
| TW | 201233163 A1 | 8/2012 |
| TW | 201306241 A1 | 2/2013 |

OTHER PUBLICATIONS

Bjoern Eversmann, Martin Jenkner, Franz Hofmann, Christian Paulus, Birgit Holzapfl, Roland Thewes, Armin Lambacher, Alexander Kaul, Ralf Zeitler, Matthias Merz, Alexander Kunze, Peter Fromherz, Landsiedel; "CMOS sensor array for electrical imaging of neuronal activity." IEEE International Symposium on Circuits and Systems. vol. 4. IEEE; 1999, 2005.*

(Continued)

*Primary Examiner* — Jermele M Hollington
*Assistant Examiner* — Christopher McAndrew
(74) *Attorney, Agent, or Firm* — Merchant & Gould P.C.

(57) ABSTRACT

A readout device includes a plurality of detecting circuits arranged in rows and columns to form a detecting array, and an output module. Each of the detecting circuits includes two transistors for generating a detection signal associated with impedance at a target site. Through selection of the rows and the columns of the detecting circuits, the output module outputs an output voltage signal having a magnitude positively correlated with magnitude of a selected one of the detection signals received from the detecting circuits.

2 Claims, 6 Drawing Sheets

(51) Int. Cl.
*H04N 5/357* (2011.01)
*H04N 5/3745* (2011.01)
*H04N 5/378* (2011.01)
*G01R 27/02* (2006.01)
*G01R 27/14* (2006.01)
*G01L 1/20* (2006.01)
*A61B 5/053* (2006.01)
*A61B 5/00* (2006.01)

(52) U.S. Cl.
CPC .............. *G01L 1/205* (2013.01); *G01R 27/02* (2013.01); *G01R 27/14* (2013.01)

(56) References Cited

U.S. PATENT DOCUMENTS

| | | | | |
|---|---|---|---|---|
| 4,439,693 | A * | 3/1984 | Lucas | G11C 27/026 327/100 |
| 6,522,155 | B2 * | 2/2003 | Pietsch | B60N 2/002 324/691 |
| 6,657,445 | B2 * | 12/2003 | Cresswell | G01G 19/4142 324/691 |
| 7,982,446 | B2 | 7/2011 | Noon et al. | |
| 8,344,742 | B2 * | 1/2013 | Abassi | C12Q 1/002 324/691 |
| 8,536,882 | B2 * | 9/2013 | Yeh | G06F 3/045 324/691 |
| 8,536,884 | B2 * | 9/2013 | Yeh | G06F 3/045 324/691 |
| 8,585,878 | B2 * | 11/2013 | Albu | A63B 69/0002 204/400 |
| 8,796,036 | B2 | 8/2014 | Fife et al. | |
| 2008/0129841 | A1 * | 6/2008 | Dosluoglu | H04N 5/335 348/231.99 |
| 2008/0291309 | A1 * | 11/2008 | Gruev | H04N 5/3658 348/308 |
| 2011/0026806 | A1 | 2/2011 | Bernstein et al. | |
| 2011/0211611 | A1 * | 9/2011 | Troccoli | G06K 9/0002 374/45 |
| 2012/0007611 | A1 * | 1/2012 | Yeh | G06F 3/045 324/649 |
| 2013/0193305 | A1 * | 8/2013 | Xu | H04N 5/376 250/208.1 |
| 2013/0238129 | A1 * | 9/2013 | Rose | F04B 9/10 700/258 |
| 2013/0300457 | A1 * | 11/2013 | Troccoli | G11C 8/04 326/105 |
| 2013/0320994 | A1 * | 12/2013 | Brittain | G06F 3/0416 324/537 |
| 2013/0342226 | A1 * | 12/2013 | Wang | G06F 3/045 324/691 |
| 2014/0084143 | A1 | 3/2014 | Sakano et al. | |
| 2014/0191771 | A1 * | 7/2014 | Nam | G06F 3/041 324/691 |

OTHER PUBLICATIONS

Lin et al., "A Novel Readout Circuit for an OTFD Gas Sensor with a New Front-end Trans-impedance Amplifier", *IEEE Sensors Journal*, 2011, pp. 1141-1144.

Taiwanese Search Report for corresponding Taiwanese Application No. 102143250, issued Jul. 14, 2015.

* cited by examiner

READOUT DEVICE, DUAL-FUNCTION READOUT DEVICE, AND DETECTING CIRCUIT THEREOF

CROSS-REFERENCE TO RELATED APPLICATION

This application claims priority to Taiwanese Application No. 102143250, filed on Nov. 27, 2013.

BACKGROUND OF THE INVENTION

1. Field of the Invention

The invention relates to a readout device, and more particularly to an array-type readout device, a dual-function readout device, and a detecting circuit for a readout device.

2. Description of the Related Art

In Wan-Jun Lin, Chao P. C. P., Shir-Kuan Lin, Hsiao-Wen Zan, "A Novel Readout Circuit for an OTFD Gas Sensor with a New Front-end Trans-impedance Amplifier", Sensors, IEEE, pp. 1141-1144, 2011, an impedance detecting circuit is proposed. However, the proposed impedance detecting circuit includes two operational amplifiers, resulting in a large size that is unfavorable for use in an array-type readout device. Such a large detecting circuit is only suitable for use in a single-type readout device, and may have a relatively low sensitivity and a relatively low signal-to-noise (SNR) ratio.

SUMMARY OF THE INVENTION

Therefore, an object of the present invention is to provide an array-type readout device that may have relatively good sensitivity and a relatively good SNR ratio.

According to one aspect of the present invention, a readout device capable of impedance detection comprises:
  a plurality of detecting circuits arranged in rows and columns to form a detecting array, each of the detecting circuits including:
    an output terminal, wherein the output terminals of the detecting circuits arranged in the same column are coupled to each other;
    a first transistor having a first terminal to be coupled to a voltage source, a second terminal, and a control terminal coupled to the second terminal thereof;
    a second transistor having a first terminal coupled to the second terminal of the first transistor, a second terminal to be coupled to a target site, and a control terminal disposed to receive an input voltage, wherein the second transistor is responsive to the input voltage to generate a detection signal at the second terminal thereof, the detection signal having a magnitude proportional to impedance at the target site; and
    a switch disposed to receive a row control signal that is provided to the switches of all of the detecting circuits arranged in the same row, and configured to selectively transmit the detection signal at the second terminal of the second transistor to the output terminal in response to the row control signal received thereby; and
  an output module coupled to the output terminal of each of the detecting circuits, disposed to receive a select signal, and configured to output an output voltage signal having a magnitude positively correlated with magnitude of one of the detection signals received thereby and selected according to the select signal.

Another object of the present invention is to provide a dual-function readout device.

According to another aspect of the present invention, a dual-function device comprises:
  a first transistor having a first terminal to be coupled to a voltage source, a second terminal, and a control terminal coupled to the second terminal thereof;
  a sensor configured to sense a target and to generate a sensor current corresponding to the target; and
  a dual-function readout circuit including:
    a current generating module disposed to receive an input voltage, coupled to the second terminal of the first transistor, coupled to the sensor for receiving the sensor current therefrom, to be coupled to a target site, and configured to selectively generate one of a first current and a second current, the first current being generated according to the input voltage and to be provided to the target site for generation of a detection signal having a magnitude proportional to impedance at the target site, the second current having a magnitude positively correlated with that of the sensor current;
    an integrator capacitor coupled to the current generating module for converting the second current into an integrator voltage proportional in magnitude to the sensor current;
    a sample-and-hold module coupled to the integrator capacitor and operable to output a sensor voltage; and
    an output module coupled to the current generating module for receiving the detection signal therefrom, coupled to the sample-and-hold module for receiving the sensor voltage therefrom, and configured to convert one of the detection signal and the sensor voltage into an output current.

Yet another object of the present invention is to provide a detecting circuit capable of impedance detection.

According to yet another aspect of the present invention, a detecting circuit comprises:
  an output terminal;
  a first transistor having a first terminal to be coupled to a voltage source, a second terminal, and a control terminal coupled to the second terminal thereof;
  a second transistor having a first terminal coupled to the second terminal of the first transistor, a second terminal to be coupled to a target site, and a control terminal disposed to receive an input voltage, wherein the second transistor is responsive to the input voltage to generate a detection signal at the second terminal thereof, the detection signal having a magnitude proportional to impedance at the target site; and
  a switch disposed to receive a control signal and configured to selectively transmit the detection signal at the second terminal of the second transistor to the output terminal in response to the control signal received thereby.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
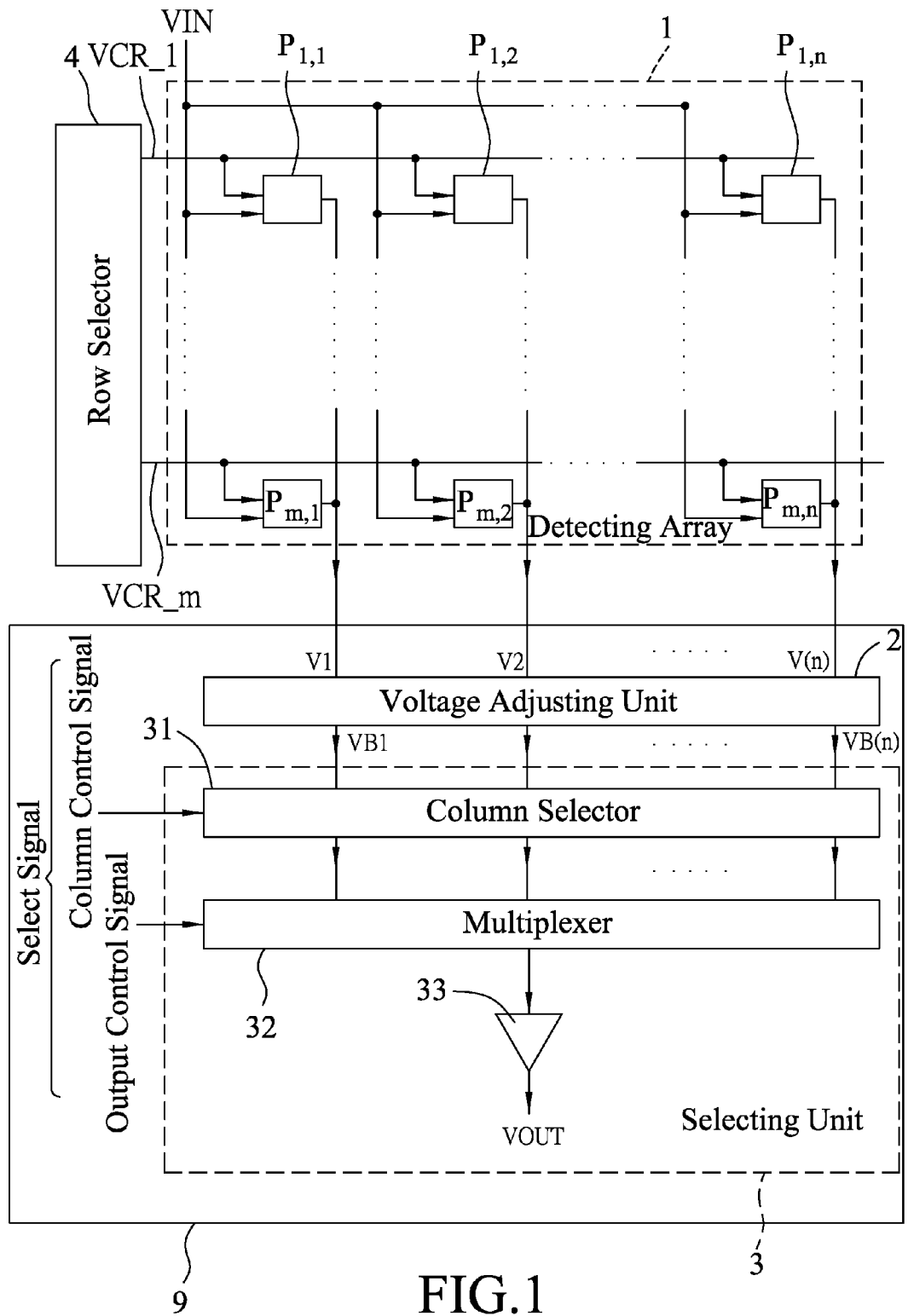
FIG. 1 is a block diagram illustrating a preferred embodiment of an array-type readout device according to the present invention.

Referring to FIG. 1, the preferred embodiment of the array-type readout device according to this invention is shown to include m×n detecting circuits $P_{1,1}$ to $P_{m,n}$ arranged in m rows and n columns to form a detecting array 1, a row selector 4, and an output module 9, where m, n are positive integers.

The row selector 4 is configured to generate m row control signals VCR_1 to VCR_m.

The detecting array 1 receives an input voltage VIN, and is coupled to the row selector 4 to receive the row control signals VCR_1~VCR_m. All of the n detecting circuits arranged in the same row receive the same one of the row control signals VCR_1 to VCR_m.

Figure 2:
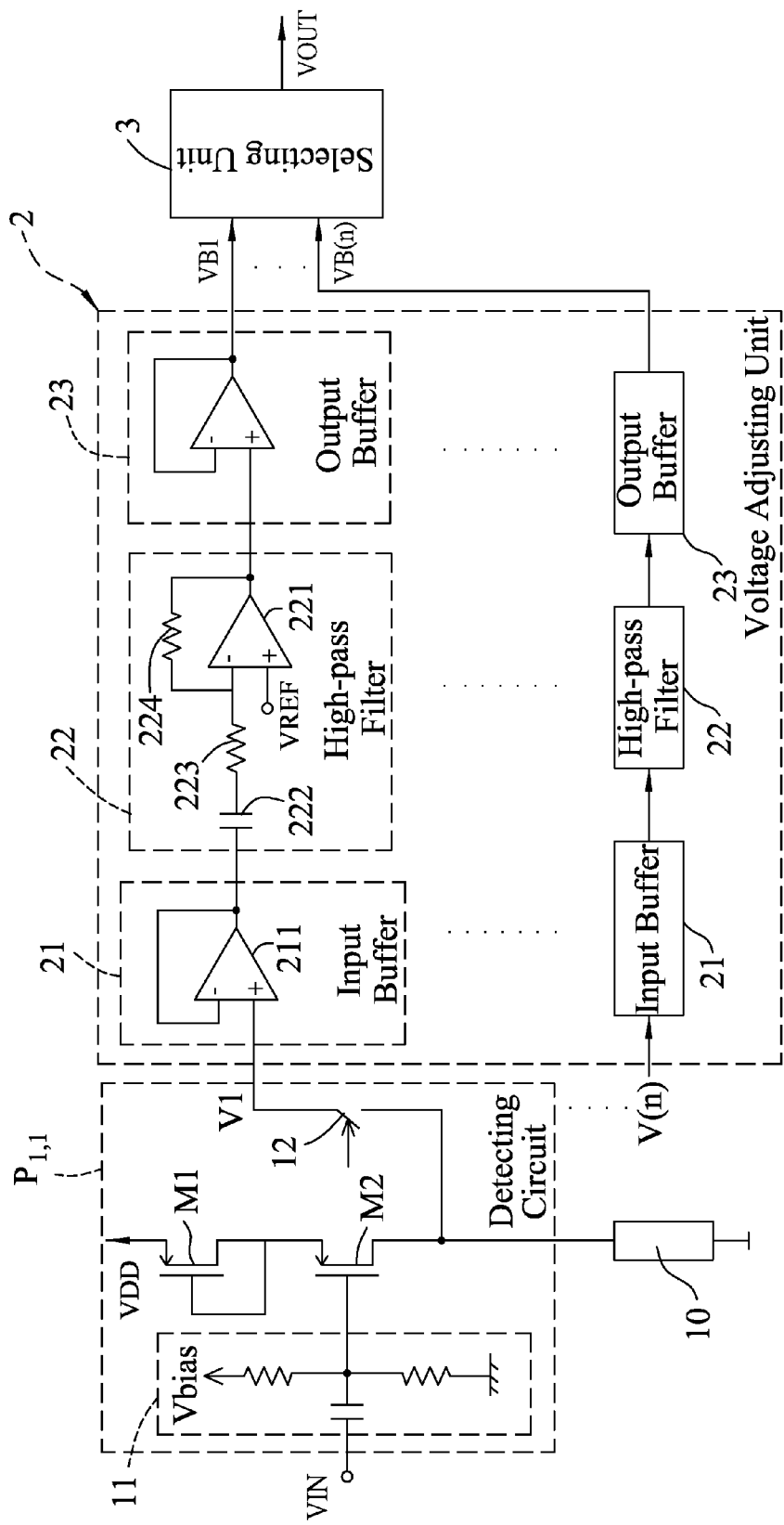
FIG. 2 is a schematic circuit diagram of the preferred embodiment of the array-type readout device.

Referring to FIG. 2, each of the detecting circuits $P_{1,1}$ to $P_{m,n}$ includes an output terminal, a first transistor M1, a second transistor M2, a switch 12 and a biasing circuit 11. It should be noted that, for the sake of clarity, only the detecting circuit $P_{1,1}$ is shown in FIG. 2.

The output terminals (e.g., V1) of the detecting circuits arranged in the same column (e.g., $P_{1,1}$ to $P_{m,1}$) are coupled to each other.

The first transistor M1 has a first terminal coupled to a voltage source VDD, a second terminal, and a control terminal coupled to the second terminal thereof.

The second transistor M2 has a first terminal coupled to the second terminal of the first transistor M1, a second terminal coupled to a target site 10, and a control terminal receiving the input voltage VIN. The second transistor M2 is responsive to the input voltage VIN to generate a detection signal at the second terminal thereof. The detection signal has a magnitude proportional to impedance at the target site 10.

In this embodiment, each of the first and second transistors M1, M2 is a P-type metal-oxide-semiconductor field-effect transistor (MOSFET) that has a source terminal serving as the first terminal, a drain terminal serving as the second terminal, and a gate terminal serving as the control terminal. However, the present invention should not be limited in this respect.

This preferred embodiment is applicable to impedance detection of human skin, that is, the target site 10 is the human skin. The detected impedance of the human skin is useful for diagnosis of skin cancers. Details of impedance detection are described hereinafter.

Figure 3:
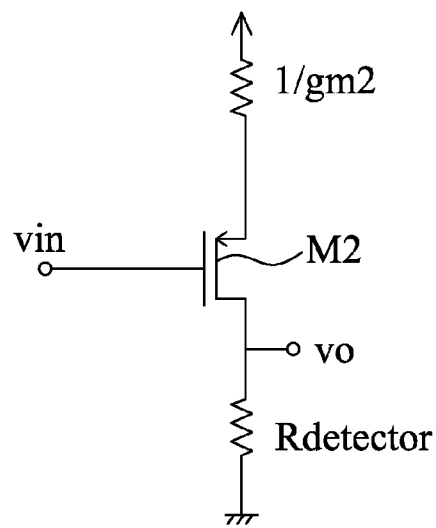
FIG. 3 is a small-signal model of a detecting circuit of the preferred embodiment of the array-type readout device.

In this embodiment, the input voltage VIN is a sine wave signal. Referring to FIG. 3, a small-signal model of the detecting circuit $P_{1,1}$ is shown to have a voltage gain Av of:

$$Av = \frac{vo}{vin} = \frac{\frac{1}{gm1}}{\frac{1}{gm1} + \frac{1}{gm2}} \times gm1 \times R \text{ detector} \qquad (1)$$

where gm1 is transconductance of the first transistor M1, gm2 is transconductance of the second transistor M2, and Rdetector is the impedance at the target site 10.

By designing width-to-length ratios (W/L) of the first and second transistors M1, M2 such that gm2>>gm1, it could be derived that:

$$Av = \frac{vo}{vin} = gm1 \times R \text{ detector} \qquad (2)$$

According to equation (2), it is evident that vo is proportional to Rdetector, and since values of gm1 and vin are known, Rdetector may be obtained by measuring a magnitude of vo.

Figure 4:
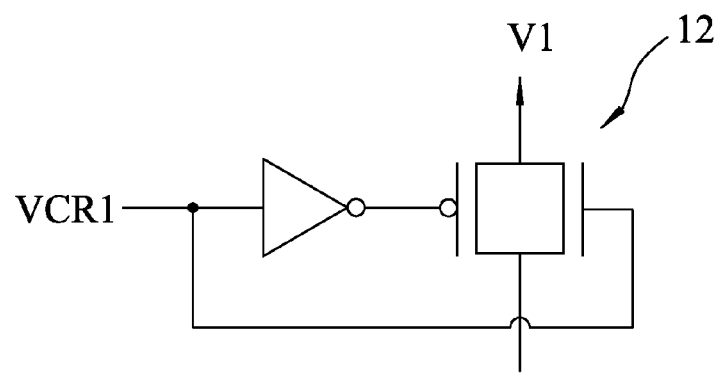
FIG. 4 is a schematic circuit diagram illustrating a switch of the preferred embodiment of the array-type readout device.

Referring again to FIG. 2, the switch 12 of each of the detecting circuits $P_{1,1}$ to $P_{m,n}$ receives the corresponding row control signal that is provided to the switches 12 of all of the detecting circuits arranged in the same row (e.g., $P_{1,1}$ to $P_{1,n}$), and selectively transmits the detection signal at the second terminal of the second transistor M2 to the output terminal (e.g., V1) in response to the row control signal received thereby. The switch 12 may be configured to have a structure as shown in FIG. 4.

The biasing circuit 11 receives a bias voltage Vbias, and is coupled to the control terminal of the second transistor M2 for provision of a direct-current (DC) working voltage thereto.

The output module 9 is coupled to the output terminal of each of the detecting circuits $P_{1,1}$ to $P_{m,n}$ (i.e., the output terminals V1 to V(n)), receives a select signal, and outputs an output voltage signal VOUT having a magnitude positively correlated with magnitude of one of the detection signals received thereby and selected according to the select signal. In this embodiment, the output module 9 includes a voltage adjusting unit 2 and a selecting unit 3, and the select signal includes a column control signal and an output control signal.

The voltage adjusting unit 2 is coupled to the output terminal of each of the detecting circuits $P_{1,1}$ to $P_{m,n}$ (i.e., the output terminals V1 to V(n)), adjusts the magnitude of each of the detection signals received thereby, and outputs adjusted signals VB1 to VB(n). Each of the adjusted signals VB1 to VB(n) corresponds to a respective one of the detection signals received thereby, and has a magnitude positively correlated with the magnitude of the corresponding one of the detection signals. In this embodiment the voltage adjusting unit 2 includes n input buffers 21, n high-pass filters 22 and n output buffers 23.

Each of the input buffers 21 receives one of the detection signals from a respective one of the columns of the detection circuits and serves to enhance driving capability of the detection signal received thereby. The input buffer 21 includes an operational amplifier 211 having a non-inverting input (+) receiving the corresponding one of the detection signals from the corresponding detecting circuit, an inverting input (−), and an output coupled to the inverting input (−) thereof.

Each of the high-pass filters 22 receives one of the detection signals from the output of a respective one of the input buffers 21, adjusts a direct-current voltage level of said one of the detection signals received thereby, and generates one of the adjusted signals having an alternating-current (AC) amplitude substantially the same as that of said one of the detection signals received thereby. Each of the high-pass filters 22 includes an operational amplifier 221, a capacitor 222, a first resistor 223 and a second resistor 224.

The operational amplifier 221 includes a non-inverting input (+) receiving a reference voltage VREF, an inverting input (−) and an output that outputs the adjusted signal. The capacitor 222 has a first terminal coupled to the output of the operational amplifier 211 for receiving the detection signal therefrom, and a second terminal. The first resistor 223 is coupled between the second terminal of the capacitor 222 and the inverting input (−) of the operational amplifier 221. The second resistor 224 is coupled between the inverting input (−) and the output of the operational amplifier 221.

Each of the output buffers 23 receives said one of the adjusted signals from a respective one of the high-pass filters 22, serves to enhance driving capability of the adjusted signal received thereby, and provides said one of the adjusted signals VB1 to VB(n) received thereby to the selecting unit 3.

The selecting unit 3 is coupled to the voltage adjusting unit 2 for receiving the adjusted signals VB1 to VB (n), receives the select signal for selecting one of the adjusted signals VB1 to VB(n), and outputs the output voltage signal VOUT having the magnitude positively correlated with the magnitude of one of the detection signals corresponding to the selected one of the adjusted signals VB1 to VB(n). In this embodiment, the selecting unit 3 includes a column selector 31, a multiplexer 32 and a buffer 33.

The column selector 31 receives the column control signal, receives the adjusted signals VB1 to VB (n) from the voltage adjusting unit 2, and is responsive to the column control signal to sequentially output the adjusted signals VB1 to VB(n) received thereby.

The multiplexer 32 receives the output control signal, receives the adjusted signals VB1 to VB(n) sequentially outputted by the column selector 31, and selects one of the adjusted signals VB1 to VB(n) received thereby according to the output control signal to serve as the output voltage signal.

The buffer 33 is coupled to the multiplexer 32 for receiving the output voltage signal, serves to enhance driving capability of the output voltage signal, and outputs the output voltage signal VOUT enhanced thereby.

Figure 5:
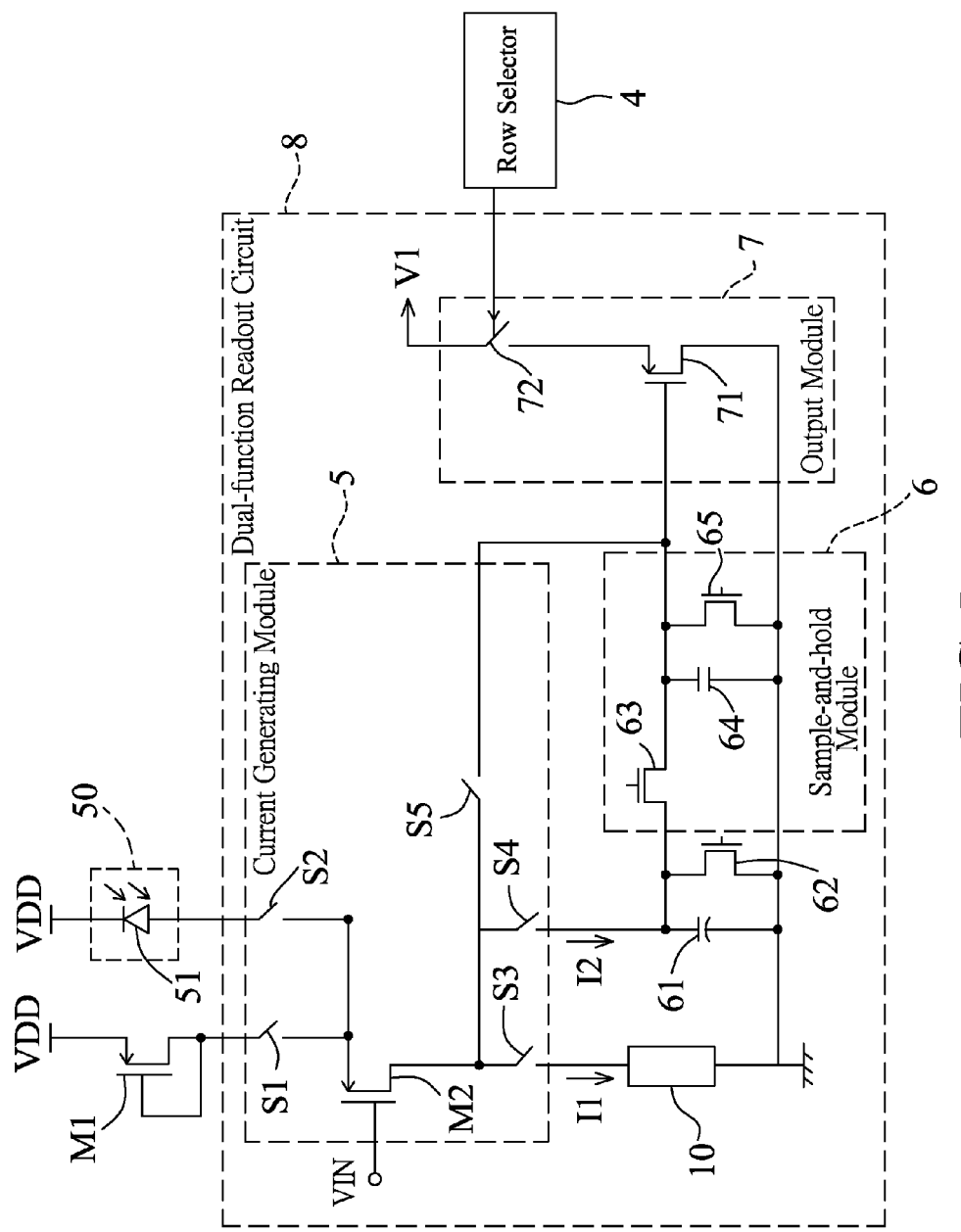
FIG. 5 is a schematic circuit diagram of a preferred embodiment of a dual-function readout device according to the present invention.

Referring to FIG. 5, a preferred embodiment of the dual-function readout device according to the present invention is shown to selectively operate in one of a first sensing mode and a second sensing mode, and includes a first transistor M1, a sensor 50 and a dual-function readout circuit 8. In this embodiment, the first sensing mode is an impedance detection mode, and the second sensing mode is a photo detection mode.

The first transistor M1 has a first terminal coupled to a voltage source VDD, a second terminal and a control terminal coupled to the second terminal thereof.

The sensor 50 is configured to sense a target and to generate a sensor current corresponding to the target. In this embodiment, the sensor 50 includes a photo sensing component 51, but should not be limited thereto. In other embodiments, the sensor 50 may include a biosensor component (not shown) configured to generate the sensor current in response to ion concentration sensed thereby. The photo sensing component 51 is a photodiode configured to generate the sensor current in response to light sensed thereby, and has a cathode coupled to the voltage source VDD, and an anode.

The dual-function readout circuit 8 includes a current generating module 5, an integrator capacitor 61, an integrator reset switch 62, a sample-and-hold module 6 and an output module 7.

The current generating module 5 receives an input voltage VIN, is coupled to the second terminal of the first transistor M1, is coupled to the sensor 50 for receiving the sensor current therefrom, is coupled to a target site 10, and selectively generates one of a first current I1 and a second current I2. The first current I1 is generated according to the input voltage VIN and is provided to the target site 10 for generation of a detection signal having a magnitude proportional to impedance at the target site 10. The second current I2 has a magnitude positively correlated with that of the sensor current. The current generating module 5 includes a second transistor M2 and first to fifth switches S1 to S5.

The second transistor M2 has a first terminal, a second terminal, and a control terminal receiving the input voltage VIN.

The first switch S1 is configured to make or break electrical connection between the second terminal of the first transistor M1 and the first terminal of the second transistor M2.

The second switch S2 is configured to make or break electrical connection between the sensor 50 and the first terminal of the second transistor M2.

The third switch S3 has a first terminal coupled to the second terminal of the second transistor M2, and a second terminal coupled to the target site 10, and makes or breaks electrical connection between the first and second terminals thereof.

The fourth switch S4 is configured to make or break electrical connection between the integrator capacitor 61 and the second terminal of the second transistor M2.

The fifth switch S5 has a first terminal coupled to the second terminal of the second transistor M2, and a second terminal coupled to the output module 7, and makes or breaks electrical connection between the first and second terminals thereof.

Figure 6:
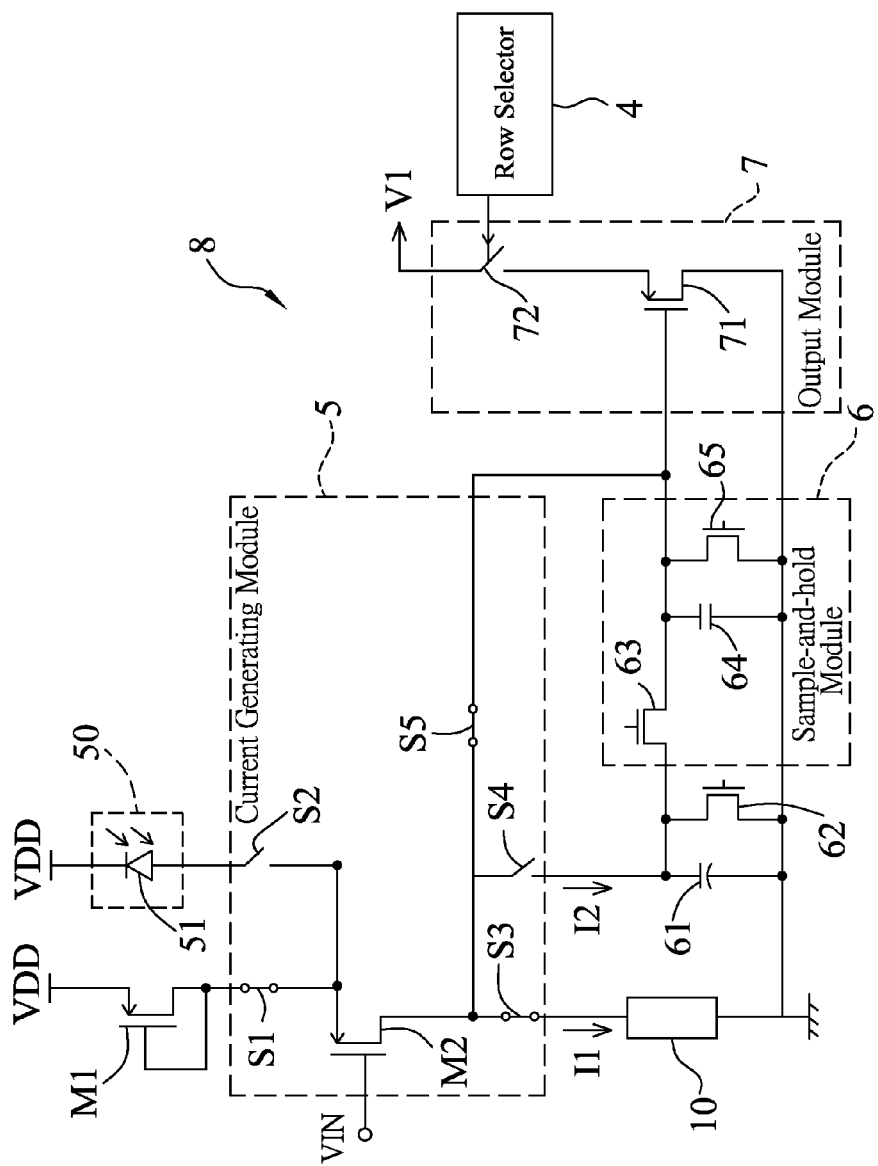
FIG. 6 is a schematic circuit diagram illustrating the preferred embodiment of the dual-function readout device operating in a first detecting mode.

Referring to FIG. 6, in the first sensing mode, the first, third and fifth switches S1, S3, S5 make electrical connections, and the second and fourth switches S2, S4 break electrical connections.

Figure 7:
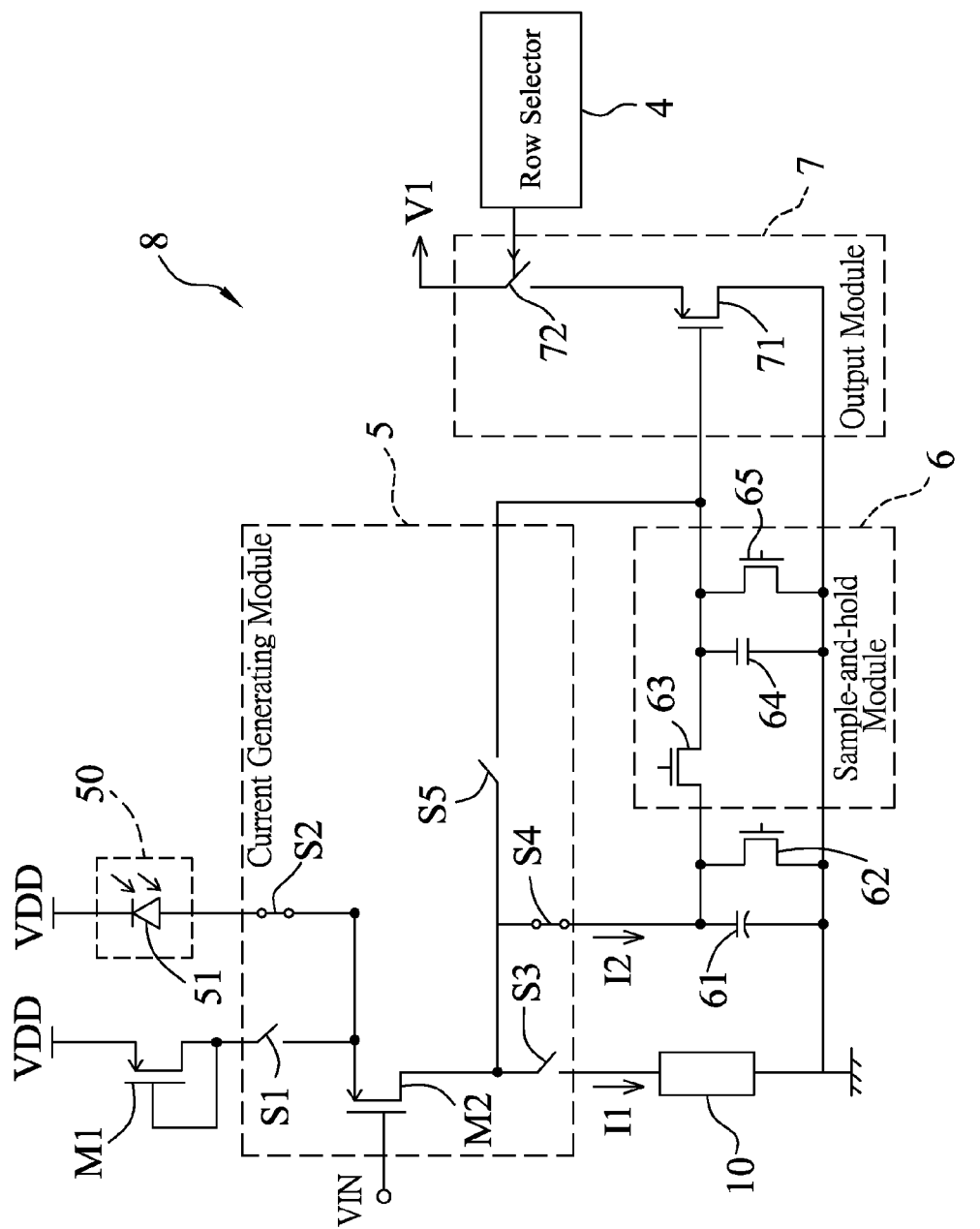
FIG. 7 is a schematic circuit diagram illustrating the preferred embodiment of the dual-function readout device operating in a second detecting mode.

Referring to FIG. 7, in the second sensing mode, the first, third and fifth switches S1, S3, S5 break electrical connections, and the second and fourth switches S2, S4 make electrical connections.

Referring again to FIG. 5, the integrator capacitor 62 is coupled to the current generating module 5 for converting the second current I2 into an integrator voltage Vint proportional in magnitude to the sensor current:

$$Vint = \frac{1}{Cint} \int_0^t I(t)dt \qquad (3)$$

where Cint is capacitance of the integrator capacitor 62, I(t) is the magnitude of the second current I2 at time t, and t is integration time.

The integrator reset switch 62 is coupled to the integrator capacitor 61 in parallel for clearing electrical charges stored in the integrator capacitor 61 when in a conducting state.

The sample-and-hold module 6 is coupled to the integrator capacitor 61 for sampling and holding the integrator voltage therefrom, is operable to output the voltage held thereby to serve as a sensor voltage, and includes a readout switch 63, a sampling capacitor 64 and a sampling reset switch 65.

The readout switch 63 has a first terminal coupled to the integrator capacitor 61 for receiving the integrator voltage therefrom, and a second terminal coupled to the second terminal of the fifth switch S5 of the current generating module 5, and is configured to make or break electrical connection between the first and second terminals thereof.

The sampling capacitor 64 is coupled between the second terminal of the readout switch 63 and a ground node for holding the voltage sampled through the readout switch 63.

The sampling reset switch 65 is coupled to the sampling capacitor 64 in parallel for clearing electrical charges stored in the sampling capacitor 64 when in a conducting state.

The output module 7 is coupled to the current generating module 5 for receiving the detection signal therefrom, is coupled to the sample-and-hold module 6 for receiving the sensor voltage therefrom, and converts one of the detection signal and the sensor voltage into an output current. It should be noted that the preferred embodiment of the dual-function readout device is applicable to the detecting array 1 of the array-type readout device of the present invention, and serves as the detecting circuit. For such application, the output module 7 includes an output terminal V1, an output transistor 71 and an output switch 72.

The output transistor 71 has a first terminal for provision of the output current, a grounded second terminal, and a control terminal for receiving one of the detection voltage and the sensor voltage. In this embodiment, the output transistor 71 is a P-type MOSFET that has a source terminal serving as the first terminal, a drain terminal serving as the second terminal, and a gate terminal serving as the control terminal.

The output switch 72 is configured to make or break electrical connection between the output terminal V1 and the first terminal of the output transistor 71. When the dual-function readout device is applied to the detecting array 1 of the array-type readout device of the present invention and serves as the detecting circuit, the output switch 72 is responsive to the row control signal from the row selector 4 to make or break electrical connection.

To sum up, the detecting circuits $P_{1,1}$ to $P_{m,n}$ of the preferred embodiments are implemented using transistors, thereby having a relatively small size compared to the aforementioned prior art, and being suitable for use in the array-type readout device. Compared to a single-type readout device, the array-type readout device is advantageous in that: even when one of the detecting circuits break down, remaining ones of the detecting circuits are still operational, and the array-type readout device has relatively higher sensitivity and a higher SNR ratio. Moreover ,by using the selecting unit 3 to output signals detected by the detecting circuits in turns, an image may be obtained after post-processing.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A readout device capable of impedance detection, said readout device comprising:
   a plurality of detecting circuits arranged in rows and columns to form a detecting array, each of said detecting circuits including:
   an output terminal, wherein said output terminals of said detecting circuits arranged in the same column are coupled to each other;
   a first transistor having a first terminal to be coupled to a voltage source, a second terminal, and a control terminal coupled to said second terminal thereof;
   a second transistor having a first terminal coupled to said second terminal of said first transistor, a second terminal to be coupled to a target site, and a control terminal disposed to receive an input voltage, wherein said second transistor is responsive to the input voltage to generate a detection signal at said second terminal thereof, the detection signal having a magnitude proportional to impedance at the target site; and
   a switch disposed to receive a row control signal that is provided to said switches of all of said detecting circuits arranged in the same row, and configured to selectively transmit the detection signal at said second terminal of said second transistor to said output terminal in response to the row control signal received thereby; and
   an output module coupled to said output terminal of each of said detecting circuits, disposed to receive a select signal, and configured to output an output voltage signal having a magnitude positively correlated with magnitude of one of the detection signals received thereby and selected according to the select signal, said output module including;
      a voltage adjusting unit coupled to said output terminal of each of said detecting circuits, and configured to adjust the magnitude of each of the detection signals received thereby, and to output adjusted signals, each of the adjusted signals corresponding to a respective one of the detection signals received thereby, and having a magnitude positively correlated with the magnitude of the corresponding one of the detection signals; and
      a selecting unit coupled to said voltage adjusting unit for receiving the adjusted signals, disposed to receive the select signal for selecting one of the adjusted signals, and configured to output the output voltage signal having the magnitude positively correlated with the magnitude of one of the detection signals corresponding to the selected one of the adjusted signals,
   wherein said voltage adjusting unit includes:
      a plurality of input buffers, each of which is configured to receive one of the detection signals from a respective one of the columns of said detection circuits;
      a plurality of high-pass filters, each of which is configured to receive one of the detection signals from a respective one of said input buffers, to adjust a direct-current voltage level of said one of the detection signals received thereby, and to generate one of the adjusted signals having an alternating-current amplitude substantially the same as that of said one of the detection signals received thereby; and
      a plurality of output buffers, each of which is configured to receive said one of the adjusted signals from a respective one of said high-pass filters, and to provide said one of the adjusted signals received thereby to said selecting unit.

2. The readout device as claimed in claim 1, wherein the select signal includes a column control signal and an output control signal, said selecting unit including:
- a column selector disposed to receive the column control signal, configured to receive the adjusted signals from said voltage adjusting unit, and responsive to the column control signal to sequentially output the adjusted signals received thereby;
- a multiplexer disposed to receive the output control signal, and configured to receive the adjusted signals sequentially outputted by said column selector, and to select one of the adjusted signals received thereby according to the output control signal to serve as the output voltage signal; and
- a buffer coupled to said multiplexer for receiving and outputting the output voltage signal.

* * * * *